United States Patent [19]

Kühle et al.

[11] 4,075,235
[45] Feb. 21, 1978

[54] N-ARYL-UREA COMPOUNDS AND HERBICIDAL COMPOSITIONS

[75] Inventors: Engelbert Kühle, Berg.Gladbach; Erich Klauke, Odenthal-Hahnenberg; Ludwig Eue, Cologne, all of Germany

[73] Assignee: Bayer Aktiengesellschaft, Leverkusen, Germany

[21] Appl. No.: 376,865

[22] Filed: July 5, 1973

[30] Foreign Application Priority Data

July 14, 1972   Germany .............................. 2234586

[51] Int. Cl.² .......................................... C07C 119/00
[52] U.S. Cl. .................................. 260/453 RW; 71/98
[58] Field of Search ...................... 260/453 R, 553 A; 71/98

[56] References Cited

U.S. PATENT DOCUMENTS

| | | | |
|---|---|---|---|
| 3,326,663 | 6/1967 | Soloway et al. | 71/98 |
| 3,344,153 | 9/1967 | Kühle et al. | 260/453 R |
| 3,681,422 | 8/1972 | Scherer et al. | 260/453 R |
| 3,726,947 | 4/1973 | Moser et al. | 260/553 A |
| 3,781,331 | 12/1973 | Kühle et al. | 71/98 |

FOREIGN PATENT DOCUMENTS 1,501,293   10/1967   France .................................. 71/98

OTHER PUBLICATIONS

Klauke et al., "Herbicidal N-[(difluorochloromethylthio)aryl]ureas," (1971) CA75 No. 98343 K, (1971).

Primary Examiner—Glennon H. Hollrah
Attorney, Agent, or Firm—Burgess, Dinklage & Sprung

[57] ABSTRACT

New N-aryl-urea compounds of the formula

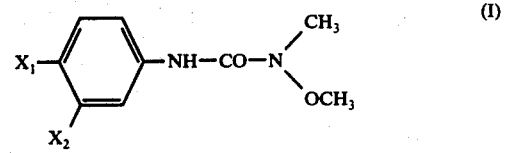

in which
  $X_1$ and $X_2$ are difluorochloromethylmercapto, chlorine or hydrogen, with either $X_1$ or $X_2$ representing difluorochloromethylmercapto;
are outstandingly effective as selective herbicides.

1 Claim, No Drawings

N-ARYL-UREA COMPOUNDS AND HERBICIDAL COMPOSITIONS

The present invention relates to certain new N-aryl-urea compounds, to herbicidal compositions containing them, and to their use as herbicides.

It is known that N-alkyl-N'-alkyl-N'-alkoxy-ureas can be used as herbicides in German Offenlegungsschrift (German Published Specification) No. 1,028,986). However, these known compounds, particularly when used in low concentrations, do not always give satisfactory herbicidal effects.

The present invention provides, as new compounds, N-arylureas of the general formula

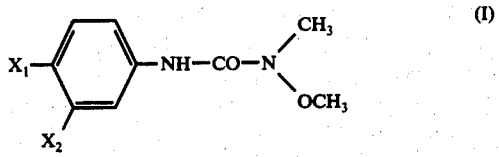

in which
X$_1$ and X$_2$ difluorochloromethylmercapto, chlorine or hydrogen, with either X$_1$ or X$_2$ representing difluorochloromethylmercapto.

The compounds of the formula (I) show good herbicidal properties. It is distinctly surprising that the active compounds according to the invention display a greater herbicidal activity and selectivity than the chemically nearest active compounds of the prior art that have the same type of action.

The present invention also provides a process for the production of a urea of the formula (I), in which
(a) an isocyanate of the general formula

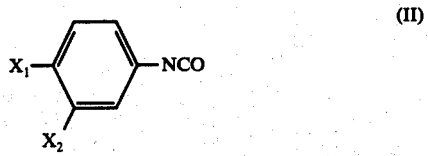

in which
X$_1$ and X$_2$ have the above-mentioned meanings,
is reacted with O,N-dimethylhydroxylamine of the formula

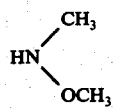

in the presence of a solvent or diluent, or
(b) an isocyanate of the general formula (II) above is reacted, in the presence of a solvent or diluent, with hydroxylamine to give an N'-hydroxyurea of the general formula

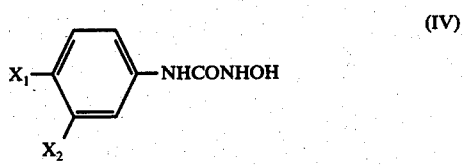

in which
X$_1$ and X$_2$ have the above-mentioned meanings,
and thereafter the compound of the formula (IV) is reacted with a methylating agent.

The course of the reaction according to process variant (a) can be represented, when using 4-difluorochloromethylmercapto-phenylisocyanate and O,N-dimethylhydroxylamine as the starting materials by the following equation:

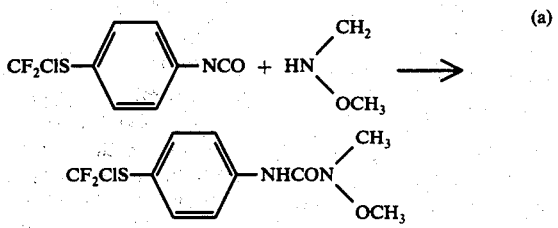

The course of the reaction according to process variant (b), when using 4-difluorochloromethylmercapto-3-chlorophenylisocyanate, hydroxylamine and methyl bromide as starting materials, can be represented by the following equation:

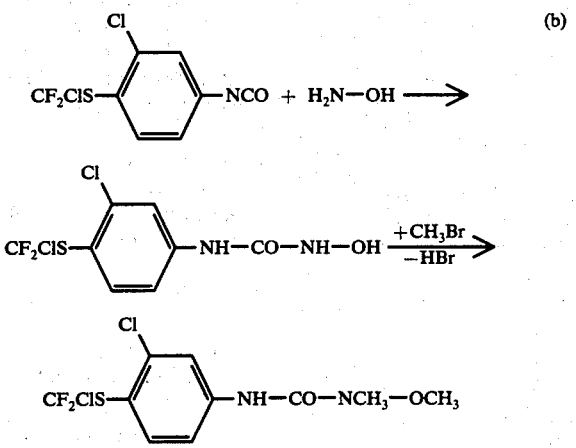

The starting materials of the formulae (II) and (III) are already known. As examples of isocyanates which can be used according to the invention there may be mentioned: 3-chloro-4-difluorochloromethylmercapto-phenylisocyanate, 3-difluorochloromethylmercapto-phenylisocyanate and 3-difluorochloromethylmercapto-4-chlorophenylisocyanate$\beta$ As methylating agents it is possible to use, for example, methyl chloride, methyl bromide and dimethyl sulphate.

Possible diluents are water, methanol and inert organic solvents, especially ethers, such as dioxane and diethyl ether, hydrocarbons, such as benzene, and chlorinated hydrocarbons, such as chlorobenzene.

The reaction temperatures can be varied over a fairly wide range; in general the reactions are effected at from 0° to 50° C, preferably from 10° to 25° C.

Approximately equimolar amounts of isocyanate and hydroxylamine or O,N-dimethylhydroxylamine are preferably employed in the process, but an excess of hydroxylamine is not detrimental. Working up is effected in the usual manner.

The preparation of the compounds of the present invention is illustrated in the following preparative Examples

Example 1

Preparation of N-(3-chloro-4-difluorochloromethylmercaptophenyl)-N'-methyl-N'-methoxyurea.

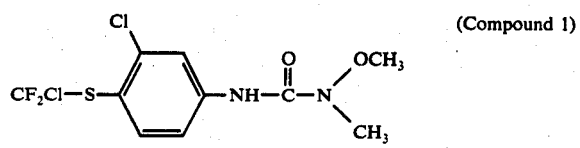

(Compound 1)

54 g of 3-chloro-4-difluorochloromethylmercaptophenylisocyanate (2/10 mol) were dissolved in 50 ml of methylene chloride and added dropwise at 5°–10° C, with vigorous stirring, to a solution of 28 g of hydroxylamine hydrochloride and 16 g of caustic soda in 200 ml of water. Thereupon, N-hydroxy-N'-(3-chloro-4-difluorochloromethylmercapto)-phenylurea crystallized out. After filtration and drying, 57 g of this product, of decomposition point 130° C, were obtained. This compound was dissolved in 300 ml. of methanol and 50 ml. of a 10-normal sodium hydroxide solution and 63 g of dimethyl sulfate were simultaneously added dropwise at 10° – 20°, while stirring. Thereupon, the reaction solution assumed a red coloration. It was stirred for 1 hour and poured into ice water; an oil, which became crystalline after standing overnight, was isolated. Yield 28 g. When recrystallized from petroleum ether, the pure product had a melting point of 66° C.

On reaction of 3-chloro-4-difluorochloromethylmercaptophenylisocyanate with O,N-dimethylhydroxylamine in dioxane, N-(3-chloro-4-difluorochloromethylmercaptophenyl)-N'-methyl-N'-methoxyurea of melting point 66° C was again obtained.

Example 2

Preparation of N-(4-difluorochloromethylmercaptophenyl)-N'-methyl-N'-methoxy-urea.

The following compound was prepared by methods analogous to those described above

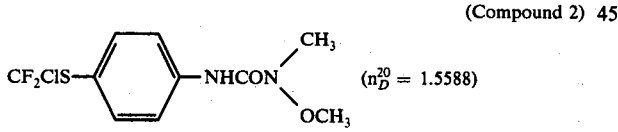

(Compound 2) ($n_D^{20}$ = 1.5588)

The compounds of the formula (I) are useful as herbicides, and can be employed in the pre-emergence or post-emergence process. Whether the compounds are used as total herbicides or as selective herbicides depends essentially on the amount used per hectare. In post-emergence used, the present compounds are distinguished, compared with those previously known, by a better selectivity in wheat. In pre-emergence use, the present compounds show good selectivity in rice.

As weeds in the broadest sense there are to be understood plants which grow in locations where they are not desired. As weeds there may be mentioned: dicotyledons, such as mustard (Sinapis), cress (Lepidium), cleavers (Galium, chickweed (Stellaria), camomile (Matricaria), gallant soldier (Galinsoga), goosefoot (Chenopodium), annual nettle (Urtica), and groundsel (Senecio), and monocotyledons, such as timothy (Phleum), bluegrass (Poa), fescue (Festuca), Goosegrass (Eleusine), foxtail (Setaria), rye grass (Lolium) and barnyard grass (Echinochloa).

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl napthalenes, chlorinated aromatic or aliphatic hydrocarbons, such as chlorobenzenes, chloroethylenes or methylene chloride, aliphatic hydrocarbons, such as cyclohexane or paraffins, for example mineraloil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicia acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The formulations in general contain from 0.1 to 95%, preferably from 0.5 to 90%, by weight of active compound.

The active compounds can be employed as such, in the form of their formulations or in the application forms prepared therefrom, such as ready-to-use solutions, emulsifiable concentrates, emulsions, foams, suspensions, wettable powders, pastes, soluble powders, dusting agents and granules. They can be employed in the usual manner, for example by squirting, spraying, atomizing, dusting, sprinkling, fumigating, watering, dressing or encrusting.

The concentrations of active compound in the ready-to-use preparations can be varied over fairly wide ranges. In general they are from 0.0001 to 10%, preferably from 0.01 to 1%, by weight.

The active compounds can also be used with good success in the ultra-low-volume (ULV) method, where it is possible to supply formulations of up to 95% active compound or even to use the active compound alone.

The present invention therefore also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides methods of growing crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the present compounds is illustrated in the following Examples.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsified was added and the concentrate was subsequently diluted with water to the desired concentration.

Test plants which had a height of about 5–15 cm were sprayed with the preparation of the active compound so that the amounts of active compound per unit area stated in the following table were applied. Depending on the concentration of the spray liquor, the amount of water used was between 1,000 and 2,000 l/ha. After three weeks, the degree of damage to the plants was determined and characterized with the values 0 - 5, which had the following meaning:

0 no effect
1 a few slightly burnt spots
2 marked damage to leaves
3 some leaves and parts of stalks partially dead
4 plants partially destroyed
5 plants completely dead.

The active compounds, the amounts used and the results can be seen from the following Table A:

Table A

| Active compound | Amount of active compound used, kg/ha | Echinochloa crus-galli | Chenopodium album | Sinapis arvensis | Matricaria inodora | Oats | Cotton | Wheat |
|---|---|---|---|---|---|---|---|---|
| CF₂Cl—S—⟨Cl⟩—NH—C(O)—N(OCH₃)(CH₃) (Compound 1) | 2<br>1<br>1<br>0.5 | 5<br>5<br>5<br>4–5 | 5<br>5<br>5 | 5<br>5<br>5 | 5<br>5<br>4 | 4–5<br>4<br>3 | 5<br>5<br>5 | 2<br>1<br>0 |
| Cl—⟨Cl⟩—NH—C(O)—N(OCH₃)(CH₃) (known) | 2<br>1<br>1<br>0.5 | 5<br>5<br>4–5 | 5<br>5<br>4–5 | 5<br>5<br>5 | 3<br>1<br>0 | 4–5<br>4<br>3 | 5<br>5<br>5 | 4<br>3<br>2 |

EXAMPLE B

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After 3 weeks, the degree of damage to the test plants was determined and characterized by the values 0–5, which had the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

The active compounds, the amounts applied and the results obtained can be seen from the following Table B:

Table B

| Active compound | Pre-emergence test Amount of active compound used, kg/ha | Echinochloa crus-galli | Portulaca oleracea | Rorippa palustre | Galinsoga ciliata | Rice |
| --- | --- | --- | --- | --- | --- | --- |
| CF$_2$Cl—S—⟨C$_6$H$_3$Cl⟩—NH—C(=O)—N(OCH$_3$)(CH$_3$) (Compound 1) | 4 | 5 | 5 | 5 | 4 | 0 |
|  | 2 | 5 | 5 | 4 | 4 | 0 |
|  | 1 | 5 | 5 | 4 | 3 | 0 |

It will be understood that the specification and examples are illustrative but not limitative of the present invention and that other embodiments within the spirit and scope of the invention will suggest themselves to those skilled in the art.

What is claimed is:

1. N-Aryl-urea compound designated N-(3-chloro-4-difluorochloromethylmercaptophenyl)-N'-methyl-N'-methoxyurea.

* * * * *

UNITED STATES PATENT AND TRADEMARK OFFICE
CERTIFICATE OF CORRECTION

PATENT NO. : 4,075,235
DATED : February 21, 1978
INVENTOR(S) : ENGELBERT KÜHLE et al It is certified that error appears in the above-identified patent and that said Letters Patent are hereby corrected as shown below:

Title page, [30] Foreign Application Priority Data,

"1972" should read -- 1973 --.

Column 4, line 35, "silicia" should read -- silicic --.

Column 5, Table A, Column entitled "Amount of active compound used, kg/ha", delete existing figures and list as follows:

2
1
0.5

2
1
0.5

Signed and Sealed this

Twenty-seventh Day of June 1978

[SEAL]

Attest:

RUTH C. MASON
Attesting Officer

DONALD W. BANNER
Commissioner of Patents and Trademarks